United States Patent [19]

Hurrell

[11] Patent Number: 4,837,441

[45] Date of Patent: * Jun. 6, 1989

[54] IONIZATION DETECTORS FOR GAS CHROMATOGRAPHY

[75] Inventor: Ronald A. Hurrell, Buckinghamshire, England

[73] Assignee: The Perkin-Elmer Corporation, Norwalk, Conn.

[*] Notice: The portion of the term of this patent subsequent to Apr. 26, 2005 has been disclaimed.

[21] Appl. No.: 922,586

[22] Filed: Oct. 24, 1986

[30] Foreign Application Priority Data

Oct. 30, 1985 [GB] United Kingdom ............... 8526765

[51] Int. Cl.[4] ............................................. G01N 27/64
[52] U.S. Cl. ............................................. 250/382; 250/372; 250/423 P
[58] Field of Search ................... 250/372, 382, 423 P, 250/423 R

[56] References Cited

U.S. PATENT DOCUMENTS

| | | | |
|---|---|---|---|
| 3,087,113 | 4/1963 | Foster | 324/464 |
| 3,134,898 | 5/1964 | Burnell et al. | 250/379 |
| 3,313,971 | 4/1967 | Nagy | 250/423 P |
| 4,063,156 | 12/1977 | Patterson | 250/382 |
| 4,304,997 | 12/1981 | Sullivan et al. | 250/379 |
| 4,733,086 | 3/1988 | Simmonds | 250/427 |
| 4,740,695 | 4/1988 | Simpson | 250/282 |

FOREIGN PATENT DOCUMENTS

| | | | |
|---|---|---|---|
| 57-94644 | 6/1982 | Japan | 324/464 |
| 1146526 | 5/1966 | United Kingdom . | |
| 2173635 | 10/1986 | United Kingdom . | |

OTHER PUBLICATIONS

"Ionization Methods for the Analysis of Gases and Vapors", Lovelock, *Analytical Chemistry*, vol. 33, No. 2, Feb. '61 pp. 162–178.

Primary Examiner—Carolyn E. Fields
Assistant Examiner—John A. Miller
Attorney, Agent, or Firm—Ronald G. Cummings; Edwin T. Grimes; Thomas P. Murphy

[57] ABSTRACT

An ionization detector for gas chromatography employs as an electron source a film (66) of gold deposited on an ultra-violet lamp (64) within a cylindrical glass body (60) closed at the ends by PTFE plugs (62 and 68). A jet anode (72) receiving effluent from a chromatographic column has its nozzle (74) adjacent the lamp (64) with a triode collector ring (78) between them. A ground wire (80) is connected to the gold film (66). Ultra-violet radiation from the lamp (64) produces a cloud of gold electrons and the consequent ionization of sample molecules from the jet (72) with a corresponding current when voltage is applied.

10 Claims, 3 Drawing Sheets

IONIZATION DETECTORS FOR GAS CHROMATOGRAPHY

This invention pertains to ionization detectors, more particularly to such detectors for use in gas chromatography.

Ionization detectors for gas chromatography are well known in the art A comprehensive survey of such detectors as of 1961 may be found in an article entitled "Ionization Methods for the Analysis of Gases and Vapors" by J. E. Lovelock, Analytical Chemistry, Volume 33, No: 2, February 1961, pages 162–178 the detectors reviewed in that article include inter alia, the cross section ionization detector, the argon detector, and the electron capture detector These detectors are characterized by the fact that each includes a source of ionizing radiation, i.e. a radio-active material The use of radio-active substances in chromatographic detectors necessarily introduces certain health risks into the laboratory and complicates such tasks as cleaning detectors after use Because of these health risks, they are also subject to certain governmental controls which complicate their application and use.

Ionization detectors have been developed which avoid the need for radio-active elements However, in many cases, these are not suitable for use as argon and electron capture detectors for various reasons, including the fact that they may require gases other than the carrier or sample. Examples are the photo-ionization detector references in the above-mentioned Lovelock article and the flame ionization detector.

More recently, an electron capture detector has been developed which utilizes a thermionic emission electron source. Such a detector is described in U.S. Pat. No. 4,304,997. However, there are certain problems inherent in a thermionic detector. One such problem is that the emitting filament may be "poisoned" by components of many samples, i.e. components may be adsorbed on the surface and thereby reduce its thermal emission.

An ionization detector has recently been developed which avoids the use of ionizing radiation, additional gases and heated filaments. This is disclosed in co-pending European application no: 85305196.9 and employs a solid photo-emissive material which is activated by ultra-violet radiation to supply the required free electrons. Specifically, this application discloses the use of antimony-cesium and multi-alkali (Na—K—Sb—Cs) alloys as photo-emitters.

The object of the present invention is a construction which increases electron production for a given amount of ultra-violet radiation, reduces chamber size to increase detector sensitivity and makes possible the use of elemental materials, rather than alloys, as photo-emissive materials. According to the invention, the photo-emissive material is either gold, aluminum or copper.

Examples of ionization detector in accordance with the invention will now be described, with reference to the accompanying drawings, in which.

It has been discovered that certain elements, in addition to the alloys proposed in the previous application, will produce electrons when irradiated by ultra-violet radiation at a wave length of 254 nanometers. At least three such elements have been experimentally located, namely gold, copper and aluminum. Of these, gold has been selected as the most practical for use in a chromatographic detector because of its low reactivity. It has also been discovered that a thin gold film will emit electrons from one surface when irradiated by ultra-violet radiation on the other surface. This makes it possible to design particularly compact and efficient detectors of the type herein described.

Figure 1:
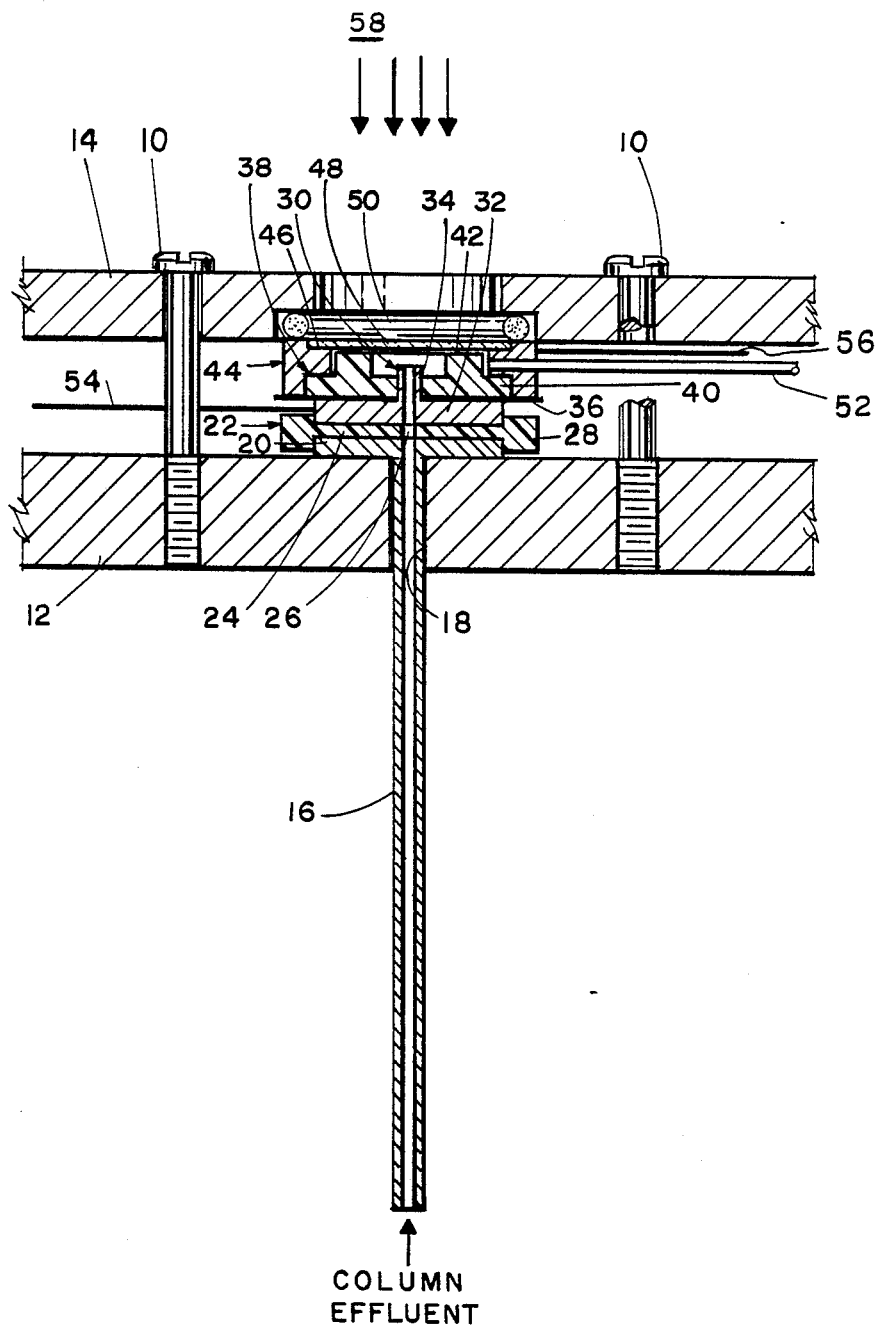
FIG. 1 is a cross section of a photo-argon detector in accordance with the present invention.

FIG. 1 illustrates an argon detector in accordance with the present invention. It comprises a disc shaped detector assembly retained by two or more screws 10 between the heater block 12 of a chromatographic column and a clamping Plate 14. A stainless steel inlet pipe 16 is connected at one end to receive the effluent from a chromatographic column (not shown). Inlet pipe 16 extends through an opening 18 in the heater block 12 and terminates at its other end in a disc shaped flange 20 which sits on the surface of the heater block 12. Positioned atop the flange 20 is an insulating disc 22 which may be, for example, of polytetrafluoroethylene (PTFE). Disc 22 includes a web 24 defining a central opening 26 aligned with the inlet pipe 16 and an outer rim 28 encircling flange 20.

Mounted against the upper surface of the web 24, as viewed in FIG. 1, is a jet 30, so named because it injects column effluent into the detector chamber. It is of stainless steel and comprises a disc body 32 and a vertical, central nozzle 34 aligned to receive and discharge column effluent from the inlet pipe 16.

Mounted atop the disc body 32 is a thin, insulating washer 36 which may be, for example, of PTFE film, upon which is positioned a PTFE bushing 38 comprising a disc 40 and an up-standing rim 42 surrounding the nozzle 34 A stainless steel ring 44 encircles the bushing 38 to form the outer wall of the detector body. It includes an inwardly directed flange 46. Flange 46 is recessed from the bottom surface of the ring 44 to enclose the disc 40 of the bushing 38 and from the upper surface to receive a thin, quartz disc window 48. An O-ring 50 maintains the elements in clamped sealed relationship. An outlet pipe 52 extends through the ring 44 to exhaust column effluent from the detector. Electrical leads 54, 56 are connected, respectively, to the jet element 30 and the ring 44.

A very thin film of gold is deposited upon the inner surface of the window 48. An ultra-violet lamp (not shown) is positioned to direct ultra-violet radiation 58 onto the upper surface of window 48. It has been discovered that, quite unexpectedly, the gold film on window 48, when irradiated from above with ultra-violet radiation having a wave length of 254 nanometers, will emit electrons from its lower surface into the chamber surrounding the nozzle 34. This results in a cloud of electrons in the detection chamber. When argon (or a similarly acting gas such as helium) is used as the carrier to elute samples from the chromatographic column, the argon atoms are raised to their metastable state by electron collisions and then ionize the sample molecules, as explained in the co-pending application referred to above and by Lovelock. With a potential applied by leads 54 and 56 between the jet nozzle 34 and the ring 44, a current flow is produced which is then amplified and recorded in the conventional manner for such a detector.

The unexpected ability of gold to emit electrons when irradiated with ultra-violet has been further exploited to produce a cross section detector. In accordance with the present invention, a gold film is irradiated from one side so as to emit electrons from the other in the same manner previously described. The cross section detector utilizing such an emitter has been made in the form of a triode, as disclosed by Lovelock, supra. A triode inherently gives a better signal/noise ratio than a diode. This is because the ions that are left when the electrons have been removed are collected so that the actual signal current in the collector is much smaller than the total current flow between the emitter and the jet.

Figure 2:
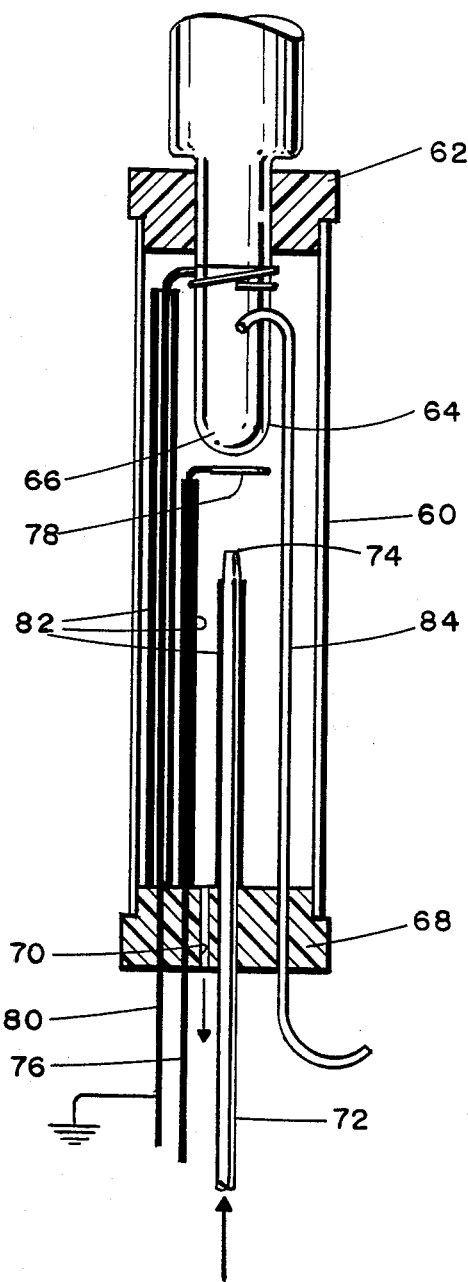
FIG. 2 is a cross section of a triode detector in accordance with the invention, particularly useful as a cross section detector.

Referring now to FIG. 2, there is illustrated a cross section detector constructed in accordance with the present invention. It comprises a cylindrical glass body 60 having a PTFE plug 62 at one end through which extends the envelope of an ultra-violet lamp 64 upon which is deposited a gold film 66. The opposite end of the cylindrical body 60 is closed by a PTFE plug 68 which defines an exhaust opening 70 and other unreferenced openings permitting the entrance of certain conductors and conduits. These include a central jet anode 72 which receives the effluent from a chromatographic column as illustrated by the arrow and has its nozzle 74 in proximity to the lamp 64. A collector wire 76 also extends through the plug 68 and is formed at its end into a triode collector ring 78 between the nozzle 74 and the lamp 64. A ground wire 80 also extends through plug 68 and is connected at its upper end to the gold film 66. Insulating sleeves 82 surround these conductors, namely the anode 72, the collector 76, and the ground wire 80. A purge line 84 also extends through the plug 68 and has its outlet end positioned closely adjacent the lamp 64.

By applying a gold film directly to the surface of the ultra-violet sources, maximum coupling is achieved between the source and the electron emitter. This, of course, serves to maximize the efficiency of the detector.

Figure 3:
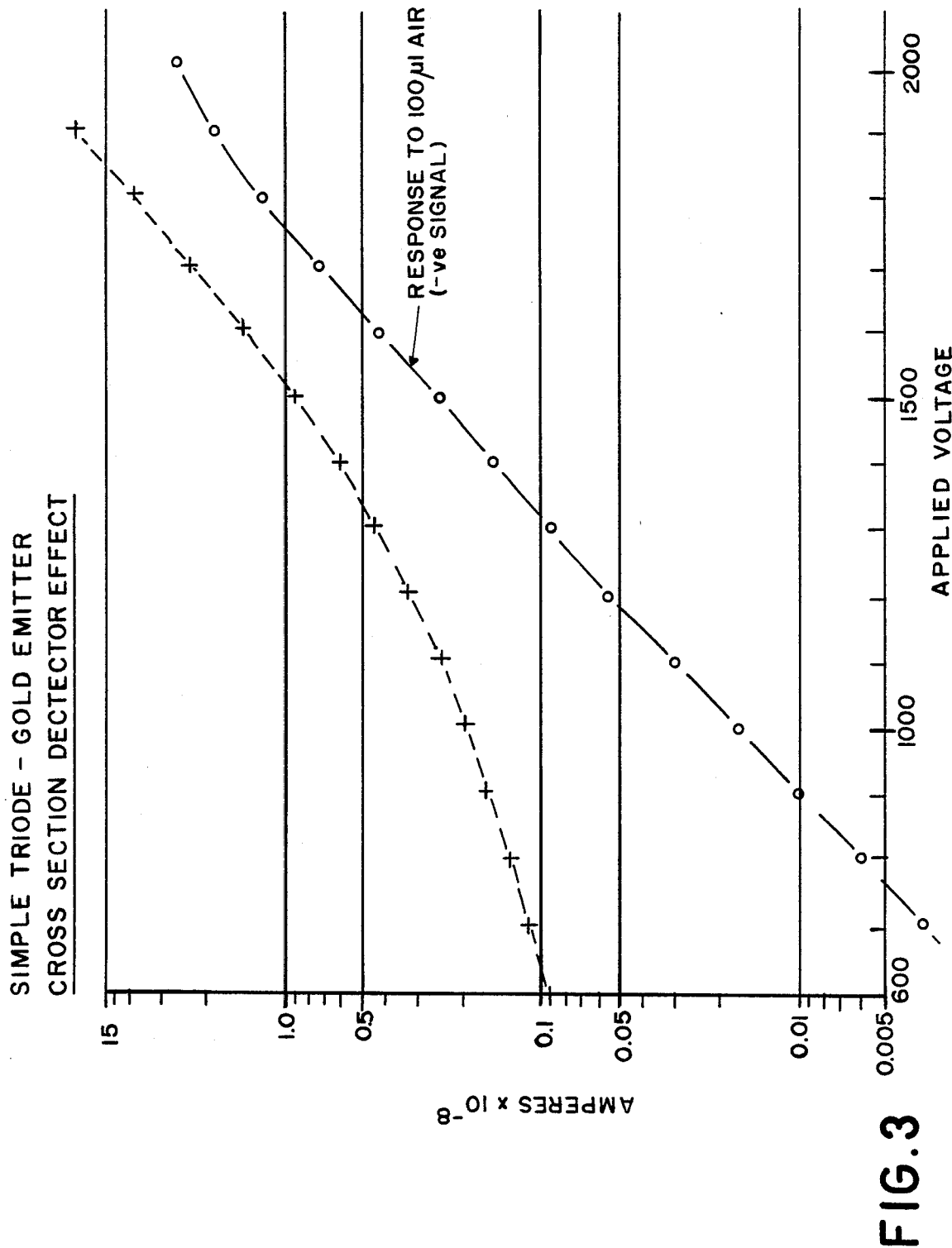
FIG. 3 is a graph showing the response curves of the detector of FIG. 2.

In FIG. 3 there is illustrated the output of the detector of FIG. 2 over a voltage range of approximately 1,000 to 2,000 volts. There is illustrated in FIG. 3 the curve of the standing current versus the applied voltage and also the curve of the diminution of standing current in response to the injection of 100 micro-liters of air. It should be noted in particular that, in the range between 1,500 and 1,800 volts, a 100 micro-liter sample of air was able to reduce the standing current by approximately twenty five percent. This indicates a very efficient cross section detector. In an actual example, the 100 micro-liter sample of air was carried in a flow of 100 ml per minute of argon and was purged by 140 ml per minute so that the sample diluted in 240 ml per minute of gas. This triode may be used to detect oxygen and nitrogen. The limit of detection is on the order of 10 micro-liters of air or nitrogen. The sensitivity is of the same order as would be expected from a hot wire detector employing helium as the carrier gas.

I claim:

1. In an apparatus for analyzing an unknown substance in a gaseous or vapor phase, a sample of which is entrained in a rare gas carrier, a detector comprising:
   a detection chamber with associated flow passages for influx and outlet of the gas and entrained sample;
   photoemissive means for emitting electrons for raising atoms of the rare gas carrier to a metastable state such that collision of said metastable atoms with molecules of said sample effects ionization of said sample molecules, said photoemissive means comprising a solid photo-emitter element of gold, aluminum or copper, said photo-emitter being positioned adjacent said chamber;
   means for irradiating said photo-emitter element with ultra-violet radiation to cause emission of electrons so as to raise atoms of the rare gas carrier to a metastable state such that collision of said metastable atoms with molecules of said sample effects ionization of said molecules; and
   means for impressing an electrical potential across said chamber.

2. A detector according to claim 1 wherein the irradiating means comprises a wall member defining a portion of the detection chamber, and the photo-emitter is deposited as a layer on the wall member.

3. A detector according to claim 2 wherein the photo-emitter is gold.

4. A detector according to claim 3 wherein the wall member is transparent to the ultra-violet radiation and the gold layer is on the chamber side of the wall member.

5. A detector according to claim 4 wherein the chamber is disc shaped and comprises an annular, electrically conductive jet enclosed by a housing and configured to release therein the effluent from a chromotogrphic column, the wall member closes the chamber and the electrical potential is applied between the housing and the jet.

6. The detector according to claim 4 wherein the detection chamber is formed by a cylindrical housing and a generally cylindrical ultra-violet source forming the wall member and co-axially enclosed by the housing.

7. A detector according to claim 6 further comprising a tubular electrode arranged to inject chromotographic column effluent into the chamber, and grounding means connected to the gold layer on the wall member.

8. A detector according to claim 7 further comprising a triode collector between the tubular electrode and the gold layer.

9. A detector according to claim 8 wherein the triode collector is a substantially circular loop.

10. A detector according to claim 9 wherein the tubular electrode and triode collector loop are substantially co-axial with the housing and ultra-violet source.

* * * * *